(12) United States Patent
Lott et al.

(10) Patent No.: US 7,790,146 B2
(45) Date of Patent: Sep. 7, 2010

(54) HIGH SUNSCREEN EFFICIENCY WATER-IN-OIL EMULSION

(76) Inventors: Dennis Lott, 2080 N. Oceanshore Blvd., Flagler Beach, FL (US) 32136; Kelly Lewellen, 2080 N. Oceanshore Blvd., Ormond Beach, FL (US) 32136; Glenn Wiener, 18 River Ridge Trail, Ormond Beach, FL (US) 32174

( * ) Notice: Subject to any disclaimer, the term of this patent is extended or adjusted under 35 U.S.C. 154(b) by 280 days.

(21) Appl. No.: 12/084,908

(22) PCT Filed: Nov. 13, 2006

(86) PCT No.: PCT/US2006/044110

§ 371 (c)(1),
(2), (4) Date: May 13, 2008

(87) PCT Pub. No.: WO2007/059091

PCT Pub. Date: May 24, 2007

(65) Prior Publication Data

US 2009/0232751 A1    Sep. 17, 2009

Related U.S. Application Data

(63) Continuation-in-part of application No. 11/052,397, filed on Feb. 7, 2005, now Pat. No. 7,309,481.

(51) Int. Cl.
*A61K 8/00* (2006.01)
*A61K 8/18* (2006.01)
*A61K 8/02* (2006.01)
*A61Q 17/04* (2006.01)

(52) U.S. Cl. ............... 424/59; 424/60; 424/401; 514/937; 514/938; 514/844

(58) Field of Classification Search ............ 424/59; 252/309
See application file for complete search history.

(56) References Cited

U.S. PATENT DOCUMENTS 6,015,548 A * 1/2000 Siddiqui et al. ............ 424/59

* cited by examiner

*Primary Examiner*—Johann R Richter
*Assistant Examiner*—David M Browe
(74) *Attorney, Agent, or Firm*—Louis C. Paul & Associates, PLLC

(57) ABSTRACT

The present invention relates to highly stable water-in-oil sunscreen emulsions that provide a high sunscreen efficiency ("SE") having a sun protection factor ("SPF") of X, where X is at least about 15, and having a sunscreen efficiency ("SE") of at least 2, preferably at least 3, where SE is the ratio of SPF over the total weight percentage of sunscreen actives based on the total weight of the composition. The emulsions of the present invention provide photoprotection for the period corresponding to the labeled SPF throughout the period of exposure to natural sunlight and comprises (i) at least one sunscreen active and (ii) an alkyl dimethicone copolyol emulsifier in which the water-soluble, alkyl-soluble and silicone-soluble groups of the dimethicone copolyol are in specific ratios to each other. Preferably, the high SE water-in-oil emulsion comprises both a UV-A sunscreen and UV-B sunscreen. More preferably, the combination of sunscreen actives is photostable.

39 Claims, No Drawings

HIGH SUNSCREEN EFFICIENCY WATER-IN-OIL EMULSION

CROSS-REFERENCE TO RELATED APPLICATIONS

This is a continuation-in-part U.S. patent application Ser. No. 11/052,397 filed Feb. 7, 2005, now U.S. Pat. No. 7,309,481 the disclosure of which is incorporated herein by reference.

STATEMENT REGARDING FEDERALLY-SPONSORED RESEARCH OR DEVELOPMENT

Not Applicable.

FIELD OF INVENTION

The field of invention of the present invention relates to high performance sunscreening emulsions that provide a high sunscreen efficiency, highly stable water-in-oil emulsions having a sun protection factor ("SPF") of X, where X is at least about 15, and having a sunscreen efficiency ("SE") of at least 2, preferably at least 3, where SE is the ratio of SPF over the total weight percentage of sunscreen actives based on the total weight of the composition. We have surprisingly and unexpectedly found that by choosing a specific alkyl dimethicone copolyol emulsifier, heretofore commercially unavailable, a high level of photoprotection can be achieved with lower levels of sunscreen actives. The high SE water-in-oil emulsions of the present invention provides photoprotection for the period corresponding to the labeled SPF throughout the period of exposure to natural sunlight and comprises (i) at least one sunscreen active and (ii) an alkyl dimethicone copolyol emulsifier in which the water-soluble, alkyl-soluble and silicone-soluble groups of the dimethicone copolyol are in specific ratios to each other. Preferably, the high SE water-in-oil emulsion comprises both a UV-A sunscreen and UV-B sunscreen. More preferably, the combination of sunscreen actives is photostable, by which is meant an emulsion that provides an SPF of X in which each of the sunscreen actives does not photodegrade to a concentration of less than 70%, preferably not less than 75%, and more preferably not less than 80% of their initial concentration after exposure to a Minimal Erythemal Dose Y of ultraviolet radiation ("UVR") from natural sunlight, where Y is about ½X, to a maximum of 15.

BACKGROUND OF INVENTION

Commercially-available sunscreen products are often formulated as emulsions. Emulsions are two-phased, sometimes three-phased, systems of materials that are immiscible in each other. Two-phased emulsions are commonly classified as water-in-oil or oil-in-water, where the latter-mentioned phase is the continuous, outer part of the emulsion. The continuous phase need not comprise the majority by weight of the emulsion composition. By their very nature, emulsion systems are unstable; in time, all emulsions will separate into their constituent parts. Emulsifiers are therefore added to these systems to maintain stability. By "emulsion stability" is meant a system in which the oil and water phases do not separate within a period of at least 3 years.

Sunscreen products absorb a certain percentage of light over a specified spectrum. The SPF listed on sunscreen products is related to this percentage and is intended to communicate the amount of erythemal UVR attenuation. Theoretically, the numeric SPF value tells the user that he or she is protected X times longer than without sunscreen where X is the labeled SPF. For example, an SPF 30 product would, theoretically, absorb 96.7% of erythemal UVR and allow about 3.3% of unattenuated erythemal UV light to reach the skin. The user of such an SPF 30 product would conclude that he or she could stay out in the sun 30 times longer than without the sunscreen. The actual amount of protection from a particular sunscreen product depends on factors including the skin type of the user, the amount applied and frequency of re-application, time of day and season, amount of sunscreen active(s) absorbed by the skin, amount of sunscreen active(s) removed from the skin (e.g., by perspiration, swimming), and photodegradation of the active(s) themselves.

The most common effect of UVR exposure is erythema, or sunburn. In 1987, the Commision Internationale de l'Éclarage adopted a reference standard, Minimal Erythemal Dose ("MED"), which indicates the minimum dose of UVR that will produce a noticeable reddening of human skin that has not been previously exposed to UVR. MED is related to skin type.

Among sunscreen emulsion products, those of the oil-in-water type are more common. This, in part, is due to aesthetic considerations; oil-in-water emulsions have a pleasant cooling feel upon application, similar to that of water. Oil-in-water emulsions are also generally considerably less expensive to manufacture than water-in-oil emulsions of a similar SPF. Oil-in-water emulsions also suffer from a well-known disadvantage—the water-soluble emulsifiers used in oil-in-water emulsions are detergents which remove oil from the skin, including oil-soluble sunscreens contained in the oil phase of sunscreen emulsion products. As a consequence, the efficacy of an oil-in-water sunscreen emulsion in providing protection from damaging ultra-violet radiation ("UVR") is diminished as soon as the emulsion comes into contact with water (e.g., from moisture, perspiration or swimming.)

In contrast, water-in-oil sunscreen emulsions also referred to as "invert emulsions"—use water-insoluble emulsifiers. Because these emulsifiers are not detergents, water-in-oil sunscreen emulsions confer a degree of water resistance; they are less easily removed from the skin. Consequently, given equal amounts of sunscreen actives, water-in-oil sunscreen emulsions typically have a higher SPF than oil-in-water sunscreens. However, it is well-known to those of ordinary skill in the art that it is difficult to formulate stable invert emulsion systems. Water-in-oil emulsions, for example, often exhibit viscosity changes prior to phase separation, a phenomenon described as creaming. An emulsion that exhibits creaming is not homogenous from top to bottom, and thus is less efficacious from the perspective of consistently delivering the same, or substantially the same, desired level active ingredients with each application.

Silicone emulsifiers were developed to improve the stability of invert emulsion systems and thus delay separation of water-in-oil emulsions into their constituent oil and water phases. Silicone emulsifiers typically have less than twenty percent water-soluble groups (e.g., polyoxyalkylene), with the remainder of the emulsifier molecule being comprised of alkyl and silicone moieties. One silicone emulsifier used in water-in-oil emulsions is cetyl dimethicone copolyol, described in now-expired U.S. Pat. No. 4,698,178, and sold under the trade-name Abil EM-90 by Goldschmidt.

The use of an effective emulsifier is particularly important in sunscreens, which are often used many months, sometimes years, after production. The use of Abil EM-90 in water-in-oil sunscreen formulations is described in Examples 3, 4 and 5 of U.S. Pat. No. 6,936,241 (Col. 16, line 35-Column 17, line 35). These examples disclose the combination of at least one organic sunscreen and at least one hydrophobically-treated inorganic sunscreen. Emulsions made with Abil EM-90, however, have been observed to stratify (e.g., into layers of varying solubilities) when stored at cold temperatures. This is not observed in emulsions made with a different class of alkyl dimethicone copolyol, one in which water-soluble, alkyl-soluble and silicone-soluble groups are in specific ratios to each other. Silfsurf J-208-812, sold by Siltech LLC, is a lauryl dimethicone copolyol illustrative of the latter class of alkyl dimethicone copolyols. Prior to the current invention, the importance of the relationship between emulsifier selection and sunscreen efficiency was not realized. We have surprisingly found that the selection of an emulsifier with particular properties is critical to achieving a high level of sunscreen efficiency, and thereby decreasing the amount of sunscreen needed to achieve a desired SPF.

Emulsion stability, while important, is but one of several considerations in formulating an effective sunscreen composition. Equally, if not more important, is the selection of a combination of sunscreen actives that is photostable throughout the UVB and UVA spectra (i.e., from 290-400 nm) under conditions of actual use (i.e., in natural sunlight as opposed to under artificial spectra generated by a solar simulator).

Many sunscreen actives are not photostable. It is well-known to those of ordinary skill that certain organic sunscreens are oxidatively, or photooxidatively, unstable. For example, the photoinstability of avobenzone is described in U.S. Pat. Nos. 5,576,354 and 5,993,789. Pending U.S. patent application Ser. No. 10/887,464, now Publication No. 2005/0025727, describes the photoinstability of octinoxate, octisalate and homosalate. Examples 3, 4 and 5 in U.S. Pat. No. 6,936,241 each teach a water-in-oil sunscreen emulsion comprising cetyl dimethicone copolyol (Abil EM-90) and a photolabile sunscreen—octisalate. One of these examples comprises a second photolabile organic sunscreen, avobenzone. A technical brochure for Silfsurf J-208-812 discloses a water-in-oil sunscreen emulsion containing three sunscreens, two of which—octisalate and octyl methoxycinnamate—are not photostable. The weight percentage of three sunscreen actives in the emulsion made with Silfsurf J-208-812 is 17.5 and produce an expected SPF of less than about 30; it is not a high SE product according to the present invention.

Photoinstability is problematic for several reasons. First, photodegradation of sunscreen actives results in lesser amounts of effective sunscreen being present over the exposure time. A photolabile sunscreen blend therefore provides a lesser degree of photoprotection than is indicated by labeled SPF. Second, photodegradation reactions generate free radicals, which are associated with adverse health consequences, including damage to DNA and other cellular molecules. This is even more of a concern since breakdown products of photolabile sunscreens have been reported to penetrate the skin and be absorbed systemically.

U.S. Patent Application Publication No. 2004/0047818 discloses a sunscreen composition comprising avobenzone, less than 1% octocrylene (weight/weight), and a diester or polyester of naphthalene dicarboxylic acid. None of the sunscreen compositions taught in Publication No. 2004/0047818 comprise the triplet combination of avobenzone, octocrylene and oxybenzone alone, with no substantial amount of other photodegradable sunscreen actives, or with substantially no other sunscreen active present.

U.S. Patent Application Publication No. 2004/0166070 discloses non-pilling UV-photoprotecting alcoholic sunscreen gels comprising acrylates/$C_{12}$-$C_{22}$ alkylmethacrylate copolymer and an effective amount of at least one UV-A and/or UV-B screening agent where the screening agent comprises avobenzone, octocrylene, oxybenzone and/or octyl salicylate. Lower monohydric alcohols, most commonly ethanol and isopropanol, are used in the alcohol sunscreen gel compositions disclosed in this application. Example 1 discloses an ethanolic sunscreen gel containing acrylates/$C_{12}$-$C_{22}$ alkylmethacrylate copolymer in combination with four sunscreens (avobenzone, octocrylene, oxybenzone and octyl salicylate). Embodiments of the present invention do not contain one or more elements of the sunscreen composition disclosed in Publication No. 2004/0166070 including, but not limited to, the following: (i) the emulsion system of the present invention may be essentially free of lower monohydric alcohols or free of lower monohydric alcohols; (ii) the present invention may be essentially free of, or free of, acrylates/$C_{12}$-$C_{22}$ alkylmethacrylate copolymer in an effective non-pilling amount used to thicken (i.e., gel) a low molecular weight alcohol (i.e., $C_1$-$C_4$ alcohol).

U.S. Patent Application Publication No. 2005/0013781 discloses photoprotective compositions comprising one or more sunscreens and one or more "optimizing agents" which are defined as diols, alcohols, glycols, polyhydric alcohols as well as derivatives or combinations thereof that optimize SPF, Protection Factor A, Boots Star Rating, polarity, critical wavelength or photostability (or any combinations of the foregoing) of the oil phase, water phase, both phases of the composition, or the final sunscreen formulation. Polyhydric alcohols, in particular certain glycols, are disclosed in this application as "optimizing agents". Publication No. 2005/0013781 also discloses over thirty sunscreens, including avobenzone, octocrylene and oxybenzone. Table 21 discloses a composition comprising five sunscreens (homosalate, octyl salicylate, oxybenzone, octocrylene and avobenzone) in combination with two optimizing agents (1,2 octanediol and neopentyl glycol). The photostable water-in-oil emulsions of the present invention are, in preferred embodiments, substantially free of substantial amounts of "optimizing agents", preferably substantially free of "optimizing agents", and more preferably free of "optimizing agents."

Where sunscreen emulsions have a lower SE—due, for example, to the type of emulsion (e.g., oil-in-water vs. water-in-oil), emulsion instability, photoinstability of sunscreens in the emulsion, or a combination of the above—consumers can be mislead. Labeled SPF may not be indicative of the photoprotection actually provided, causing consumers to believe, mistakenly, that they can safely stay out in sun for longer periods of time than that for which the sunscreen actually provides protection. The adverse consequences of overexposure to UVR when wearing a less efficient sunscreen product (e.g., one not having an SE of at least 2) are not limited to sunburn but include potentially more serious long-term health effects, including exposure to harmful breakdown products of unstable sunscreen actives. Accordingly, there remains a long-felt but unmet need for a sunscreen emulsion that provides a high sunscreen efficacy, one with an SE value of at least 2, and preferably at least 3. Preferably, such a sunscreen emulsion would contain a photostable combination of sunscreen actives as well as resistant to removal by perspiration or from water activities. It would also have good long-term emulsion storage stability over a wide temperature range for extended periods of time. This need is met by the present invention.

Prior to the present invention, water-in-oil sunscreen emulsions using a photostable sunscreen blend (one containing avobenzone, octocrylene and oxybenzone) were observed to stratify resulting in less than optimal ratios of the sunscreens to each other and, consequently, a lower SE than that of the present invention. Surprisingly, and unexpectedly, the combination of photostable sunscreens and alkyl dimethicone copolyol, where the alkyl-soluble, water-soluble and silicone-soluble groups are in specified ratios to each other, results in sunscreen compositions having a greater SE than had been previously available. The high SE water-in-oil emulsions of the present invention do not stratify over a wide range of temperatures or over extended periods of time and provide consumers with a level of predictable, photostable, photoprotection heretofore not achieved.

SUMMARY OF THE INVENTION

The present invention relates to novel water-in-oil sunscreen emulsions having a sunscreen efficiency ("SE") of at least 2, preferably at least 3, that provide an SPF X. Preferably X is at least about 15, more preferably X is at least about 30. The high SE water-in-oil emulsions of the present invention comprise at least one sunscreen active and an effective emulsifying concentration of an alkyl dimethicone copolyol corresponding to the Formula A:

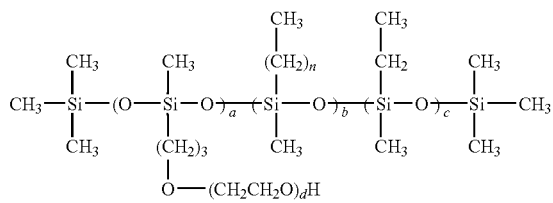

wherein;
a is an integer ranging from 2 to 10;
b is an integer ranging from 2 to 10 such that b/a greater than or equal to 1, but less than 2.5;
c is (a+b) times x, wherein x is 1.5 to 2.5;
d is an integer ranging from 6 to 12;
n is an integer ranging from 11 to 14.

In a preferred embodiment, the high SE water-in-oil emulsion contains both a UV-A sunscreen and a UV-B sunscreen, where sunscreen combination is photostable, by which is meant each of the sunscreen actives in the sunscreen combination photodegrades to a concentration of not less than 70%, preferably not less than 75%, and more preferably not less than 80% of their initial concentration after exposure to Y MEDs of UVR from natural sunlight, where Y is about ½X, to a maximum of 15 In a particularly preferred embodiment, the photostable combination of sunscreen actives is a triplet of avobenzone, octocrylene and oxybenzone.

DETAILED DESCRIPTION OF THE INVENTION

The present invention relates to novel water-in-oil sunscreen emulsions having a sunscreen efficiency ("SE") of at least 2 that provide an SPF X. Preferably X is at least about 15, more preferably X is at least about 30. The high SE water-in-oil emulsions of the present invention comprise at least one sunscreen active and an effective emulsifying concentration of an alkyl dimethicone copolyol corresponding to Formula A:

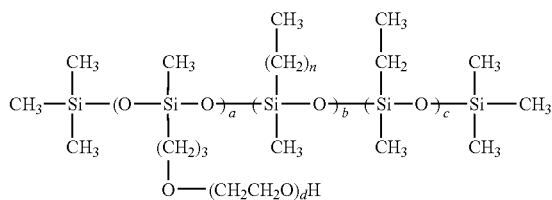

wherein
a is an integer ranging from 2 to 10;
b is an integer ranging from 2 to 10 such that b/a greater than or equal to 1, but less than 2.5;
c is (a+b) times x, wherein x is 1.5 to 2.5;
d is an integer ranging from 6 to 12;
n is an integer ranging from 11 to 14.

In a preferred embodiment, the SE is at least 3, and in a more preferred embodiment the SE is at least 4.

In a preferred embodiment, the effective emulsifying concentration emulsion does not appreciably stratify over the temperature range of from about 0° C. to about 45° C. Preferably, the effective emulsifying concentration is from about 1% to about 10%, more preferably, the effective emulsifying concentration is from about 3.0% to about 7.0%, and most preferably from about 4.5% to 5.5%. A preferred alkyl dimethicone copolyol is a lauryl dimethicone copolyol sold under the tradename Silfsurf J-208-612 by Siltech, LLC (Dacula, Ga.).

In one embodiment, the high SE water-in-oil emulsion of the present invention comprises at least one UV-A sunscreen and at least one UV-B sunscreen. In a preferred embodiment, the combination of sunscreen is photostable. As used in the present invention a "photostable" sunscreen combination is one in which each of the sunscreen actives in the combination photodegrades to a concentration of not less than 70%, preferably not less than 75%, and more preferably not less than 80% of their initial concentration after exposure to Y MEDs of UVR from natural sunlight, where Y is about ½X, to a maximum of 15.

As is well-known in the art, combinations of two or more sunscreen ingredients are used in sunscreen formulations to achieve higher levels of ultraviolet absorption or to provide absorption over a wider range of ultraviolet wavelengths than a single active ingredient. Often, the sunscreens are present in specific ratios. In a preferred embodiment, the photostable combination of sunscreen actives in the high SE water-in-oil emulsion of the present invention is a triplet of avobenzone, octocrylene and oxybenzone (the "AOO Triplet"). The ratio (weight/weight) of avobenzone to oxybenzone to octocrylene in this preferred embodiment of the present invention is preferably in the range of a:b:c, where a is from 0.5 to 5.0, b is from 0.5 to 10, and c is from 0.5 to 10. Still more preferably, a is from 1 to 3, b is from 1 to 6, and c is from 1 to 10. Once a proper ratio is selected, the sunscreen actives can be combined in sufficient amounts to achieve a desired SPF using standard formulating techniques known to persons of ordinary skill in the art to achieve an SE of at least about 2.

In a still more preferred embodiment, the high SE water-in-oil emulsion comprises the AOO Triplet and is free of diesters or polyesters of naphthalene dicarboxylic acid and/or is substantially free of substantial amounts of optimizing agents as defined in U.S. Patent Application Publication No. 2005/0013781.

In another more preferred embodiment, the high SE water-in-oil emulsion comprises the AOO Triplet and is essentially free of lower monohydric alcohol or free of lower monohydric alcohol. For purposes of the present invention, "lower monohydric alcohol" means methanol, ethanol, propanol and isoproponal, or mixtures thereof.

In yet another more preferred embodiment, the high SE water-in-oil emulsion of the present invention comprises the AOO Triplet and is essentially free of, or free of, acrylates/$C_{12-22}$ alkylmethacrylate copolymer in an effective non-pilling amount used to gel a $C_1$-$C_4$ alcohol.

In a still further more preferred embodiment, the high SE water-in-oil emulsion of the present invention comprises the AOO Triplet and is substantially free of substantial amounts of optimizing agents. Examples of optimizing agents are 1,2-pentanediol, neopentanediol, 1,2-octanediol, ethoxydiglycol, butylene glycol monopropionate, diethylene glycol monobutyl ether, PEG-7 methyl ether, octacosanyl glycol, arachidyl glycol, benzyl glycol, 1,2-hexanediol, $C_{14-18}$ glycol, $C_{15-18}$ glycol, 1,2-dodecanediol, butoxydiglycol, 1,10-decanediol, ethyl hexanediol, as well as combinations thereof. Preferably compositions of the present invention are substantially free of optimizing agents, and more preferably completely free of optimizing agents.

As used in the present application, "sunscreen active" includes both sunscreen agents and physical sunblocks. Approval by a regulatory agency is generally required for inclusion of a sunscreen active in formulations intended for contact with human skin. Thus, sunscreen active agents suitable for use in the present invention include those which are approved by the US Food and Drug Administration. Sunscreen actives that are currently approved by the FDA are listed in the Sunscreen Drug Products for Over-The-Counter Human Use Final Monograph published in the Federal Register on May 21, 1999 at Volume 64, Number 98, pages 27666-27693. Other sunscreen active ingredients are accepted for use in countries outside the US and are also considered to be within the scope of the present invention. Examples include methylbenzylidene camphor, polyacrylamidomethyl benzylidene camphor, benzylidene camphor sulfonic acid, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis-diethylamino hydroxybenzoyl benzoate, bis-benzoxazoylphenyl ethylhexylimino triazine, drometrizole trisiloxane, methylene bis-benzotriazolyl tetramethylbutylphenol, bis-ethylhexyloxyphenol methoxyphenyltriazine. Suitable sunscreen actives may be organic or inorganic and are used in safe and effective amounts in accordance with applicable regulations. Exact amounts will vary depending upon the sunscreen(s) chosen and the desired SPF.

In one embodiment, the at least one sunscreen active absorbs UVB radiation (290-320 nm). In a more preferred embodiment the at least one sunscreen active absorbs both UVB radiation and UVA radiation (320-400 nm). According to the reference values listed in the U.S. Pharmacopoeia Sunscreen Monograph (Thomson Micromedex, 2002) sunscreen actives which absorb both UVA and UVB radiation include dioxybenzone (250-390 nm), menthyl anthranilate (260-380 nm), oxybenzone (270-350 nm), sulisobenzone (260-375), titanium dioxide (290-700 nm) and zinc oxide (290-700 nm).

In a still more preferred embodiment, the high SE emulsion comprises both a UVA sunscreen and UVB sunscreen. In an even more preferred embodiment, the UVA sunscreen is a sunfilter. In a particularly preferred embodiment, the UVA sunfilter is avobenzone. In another even more preferred embodiment, the UVA sunscreen is a sunblock selected from the group consisting of titanium dioxide and zinc oxide. In a particularly preferred embodiment, the titanium dioxide and zinc oxide are micronized.

In still another even more preferred embodiment, the high SE water-in-oil emulsion of the present invention comprises a sunscreen combination of at least one UV-A sunscreen and at least one UV-B sunscreen, which combination is photostable and maintains substantially an SPF of X throughout the period of exposure and is photostable when irradiated with natural sunlight, irrespective of altitude, season, time of day, angle of the sun relative to the sample or atmospheric conditions (e.g., cloud cover).

As used in the present invention the term "photostable" sunscreen combination means a combination in which each sunscreen active does not photodegrade to less than about 70%, preferably not less than about 75%, and more preferably not less than about 80% of its initial (i.e. pre-natural UV light exposure) concentration after exposure to Y MEDs of UVR from natural sunlight, where Y is about ½ X, to a maximum of about 15. For purposes of the present invention, "pre-natural UV sunlight exposure" is intended to mean the composition just prior to being exposed to natural sunlight in a laboratory test or in actual consumer use (i.e., in the ambient environment). Incidental UV exposure in the course of manufacture and packaging of the composition is to be neglected.

"Photostability" is assessed by (i) assaying the pre-UVR exposure concentration of each sunscreen active present in the sunscreen composition by High Performance Liquid Chromatography ("HPLC"); (ii) applying a sample of the sunscreen composition at a concentration of 2 mg/cm$^2$ (a standard concentration used in SPF testing) to an uncoated microscope slide or similar non-reactive surface (e.g., glass or quartz plate); (iii) irradiating the sample in natural sunlight according to a dosing regimen as illustrated in Table 1; (iv) assaying the concentration of each sunscreen active post-UVR exposure.

TABLE 1

Dosing Regimen

| SPF | MEDs Irradiated | | | | |
|---|---|---|---|---|---|
|  | 1 | 2 | 4 | 8 | 15 |
| 2 | x | | | | |
| 4 | x | x | | | |
| 8 | x | x | x | | |
| 16 | x | x | x | x | |
| ≧30 | x | x | x | x | x |

More specifically, after the desired UVR exposure, each slide is removed from sunlight and placed in a sealed Blue Max™ polypropylene conical tube (Becton Dickinson) or similar container, and stored in an area to prevent further exposure to natural sunlight. When an irradiation series is completed, the residual content of each sunscreen active is determined via HPLC, such as the Perkin Elmer Model 200, equipped with a 785 UV/V detector, and a C18 column. A detector wavelength of 310 nm and an eluent solution of 85/15 phosphoric acid solution may be used. The sunscreen composition is extracted from the slide with isopropanol or other suitable solvent and sonicated for a minimum of 10 minutes to completely solubilize the sunscreen actives. The solution is then filtered with a 0.45 um GHP13 mm syringe filter. The above analytical procedure may be modified in a manner that would be obvious to the person of ordinary skill in the art.

Photostable high SE water-in-oil emulsions of the present invention may be prepared according to principles and techniques generally known to those skilled in the cosmetic and pharmaceutical arts. Octocrylene and oxybenzone are added under heat to a cosmetically acceptable vehicle and mixed until homogeneous. Avobenzone is then added to this mixture.

The Cosmetic, Toiletries & Fragrance Association, International Cosmetic Ingredient Dictionary and Handbook, Vol. II, p. 1364 (10th Edition, 2004) describes a wide variety of non-limiting cosmetic and pharmaceutical ingredients commonly used in the personal care industry, which are suitable for use in the photostable water-in-oil emulsions of the present invention. Examples of these ingredient classes include, but are not limited to: film formers (e.g., polymers, for aiding the film-forming properties and substantivity of the composition), antioxidants, humectants, moisturizers, pH adjusters, rheology modifiers structuring agents (e.g., beeswax, candelilla wax, paraffin), stabilizers, skin-conditioning agents, skin soothing and/or healing agents, vitamins and derivatives thereof, fragrances and preservatives. Other examples of cosmetic and/or pharmaceutical ingredients which are suitable for use in the present invention are disclosed in U.S. Patent Application Publication No. 2005/0214332.

The following examples in Table 2 are further illustrative of the present invention. The components and specific ingredients are presented as being typical, and various modifications can be derived in view of the foregoing disclosure within the scope of the invention.

bined in a main vessel and mixed while being heated to produce a uniform consistency. Phase A-1 was then added and mixing was continued. While Phase A/A-1 was mixing, Phase B ingredients were combined in a second vessel and mixed. Phase B-1 was then added to Phase B and mixing was continued. Phase A-2 was then added to the Phase A/A-1 combination. Phase B/B-1 was then added to Phase ANA-1/A-2 using slow agitation. As the emulsion began to appear uniform, agitation was increased. Processing was completed by high shear mixing.

The high SE water-in-oil sunscreen emulsions of the present invention have surprisingly been found to exhibit substantially greater emulsion stability than prior art sunscreen compositions comprising the avobenzone-octocrylene-oxybenzone sunscreen triplet and Abil EM-90 (Cetyl PEG/PPG-10/1 dimethicone). Emulsion stability was measured using a shaker/incubator. More particularly, samples in final packaging (i.e., as shipped for consumer sale) or, alternatively, in four ounce high density polyethylene bottles, were tightly packed into an appropriately-sized carton such that samples were standing in an upright position. The carton was then placed into a Lab-Line Incubator-Shaker Model 3525, a variable speed/variable temperature shaker box. The shaker/incubator was set at a speed of 175 rpm and an oven temperature of 50° C. for five hours. Shaker testing was performed initially and at the end of four, consecutive one-week intervals. The stability of the emulsions was scored on a scale of zero to five, with zero being the best and indicating

TABLE 2

| | | Example 1 (SPF 30+) | Example 2 (SPF 45+) | Example 3 (SPF 60+) |
|---|---|---|---|---|
| Phase A | Octocrylene | 4.000 | 6.000 | 8.000 |
| | Hexyldecanol | 5.000 | 4.000 | 0.000 |
| | Hydrogenated polyisobutene | 0.000 | 0.000 | 7.000 |
| | Lauryl PEG-8 dimethicone | 4.500 | 4.500 | 5.000 |
| | Ethylhexyl palmitate | 8.000 | 6.000 | 5.500 |
| | Cyclomethicone | 3.000 | 4.500 | 3.000 |
| | Cetyl dimethicone | 0.750 | 0.750 | 0.000 |
| | Methylparaben | 0.300 | 0.300 | 0.300 |
| | Propylparaben | 0.100 | 0.100 | 0.100 |
| | Benzophenone-3 | 2.500 | 4.000 | 3.500 |
| | Microcrystalline Wax | 0.250 | 0.250 | 0.250 |
| | Stearoxydimethicone, Polyethylene | 0.250 | 0.250 | 0.250 |
| | Beeswax | 0.400 | 0.400 | 0.400 |
| Phase A-1 | Hydrated silica | 3.000 | 5.000 | 3.000 |
| | Butyl methoxydibenzoylmethane | 1.000 | 1.000 | 1.000 |
| Phase A-2 | Benzyl alcohol | 1.000 | 1.000 | 0.500 |
| | PEG-7 laurate, Iodopropynyl butylcarbamate | 0.200 | 0.200 | 0.050 |
| | Dimethyl capramide | 0.000 | 2.000 | 1.250 |
| | Fragrance | 0.400 | 0.450 | 0.400 |
| | Tocopheryl acetate, retinyl palmitate, ascorbyl palmitate, silica | 0.010 | 0.010 | 0.010 |
| Phase B | Water | 63.820 | 57.770 | 58.970 |
| | Botanical Blend (40-HMX3-00)** | 0.010 | 0.010 | 0.010 |
| | Sodium chloride | 0.700 | 0.700 | 0.700 |
| | Disodium EDTA | 0.050 | 0.050 | 0.050 |
| | *Aloe barbadensis* leaf juice | 0.010 | 0.010 | 0.010 |
| Phase B-1 | Acrylates/C$_{12}$-C$_{22}$ alkylmethacrylate copolymer | 0.750 | 0.750 | 0.750 |

**Water; *Plumeria Acutifolia* Flower Extract; *Mangifera Indica* (Mango) Fruit Extract; *Psidium Guajava* Fruit Extract; *Carica Papaya* (Papaya) Fruit Extract; *Passiflora Incarnata* Fruit Extract; *Colocasia Antiquorum* Root Extract.

Examples 1-3 were prepared according to procedures for formulating sunscreen emulsion products well-known to those of skill in the art. More particularly, the following procedure was followed. All Phase A ingredients were comno change, and five being the worst and indicating complete phase separation. The results of emulsion stability testing of two formulas, Table 3 identical in all respects with the exception of the emulsifier are presented in the Table 4 below:

TABLE 3

| | | Invention | Prior Art |
|---|---|---|---|
| Phase A | Octocrylene | 6.000 | 6.000 |
| | Hexyldecanol | 4.000 | 4.000 |
| | Cetyl PEG/PPG-10/1 Dimethicone | 0.000 | 4.500 |
| | Lauryl PEG-8 Dimethicone | 4.500 | 0.000 |
| | Ethylhexyl palmitate | 6.000 | 6.000 |
| | Cyclomethicone | 4.500 | 4.500 |
| | Cetyl dimethicone | 0.750 | 0.750 |
| | Methylparaben | 0.300 | 0.300 |
| | Propylparaben | 0.100 | 0.100 |
| | Benzophenone-3 | 4.000 | 4.000 |
| | Microcrystalline wax | 0.250 | 0.250 |
| | Stearoxydimethicone, polyethylene | 0.250 | 0.250 |
| | Beeswax | 0.400 | 0.400 |
| Phase A-1 | Hydrated silica | 5.000 | 5.000 |
| | Butyl methoxydibenzoylmethane | 1.000 | 1.000 |
| A-2 | Benzyl alcohol | 1.000 | 1.000 |
| | PEG-7 laurate, Iodopropynyl butylcarbamate | 0.200 | 0.200 |
| | Dimethyl capramide | 2.000 | 2.000 |
| | Fragrance | 0.450 | 0.450 |
| | Tocopheryl acetate, Retinyl palmitate, Ascorbyl palmitate, Silica | 0.010 | 0.010 |
| Phase B | Water | 57.770 | 57.770 |
| | 40-HMX3-00 | 0.010 | 0.010 |
| | Sodium Chloride | 0.700 | 0.700 |
| | Disodium EDTA | 0.050 | 0.050 |
| | Aloe barbadensis leaf juice | 0.010 | 0.010 |
| Phase B1 | Acrylates/ $C_{12}$-$C_{22}$ alkylmethacrylate copolymer | 0.750 | 0.750 |

TABLE 4

Emulsion Stability Test Results

| | Invention | Prior Art |
|---|---|---|
| Initial | N/A | N/A |
| End Week 1 | 0 | 4 |
| End Week 2 | 0 | 4 |
| End Week 3 | 0 | 4 |
| End Week 4 | 0 | 4 |

Apart from emulsion stability and greater photoprotection, the preferred embodiments of the present invention comprising a photostable sunscreen combination provides an important consumer health benefit—minimizing the formation of potentially harmful free radicals (i.e., in photodecay products). Since individual sunscreen actives may be used in smaller quantities to achieve substantially the same SPF, lesser amounts of photoreactive sunscreens are available to form free radicals. Relatedly, as a consequence of their increased photostability, compositions of the present invention can be applied less frequently, thereby minimizing potential free radical formation.

All percentages, ratios and proportions herein are by weight, unless otherwise specified. All temperatures are in degrees Celsius unless otherwise specified. All documents cited are, in relevant, part, incorporated herein by reference.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A water-in-oil sunscreen emulsion having an sunscreen efficiency SE of at least 2 that provides a sun protection factor SPF X, where X is at least about 15, comprising
   (i) at least one sunscreen active; and
   (ii) an effective emulsifying concentration of an alkyl dimethicone copolyol corresponding to Formula A:

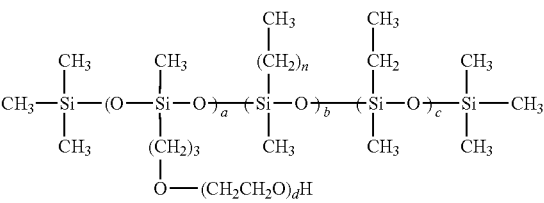

wherein
   a is an integer ranging from 2 to 10;
   b is an integer ranging from 2 to 10 such that b/a greater than or equal to 1, but less than 2.5;
   c is (a+b) times x, wherein x is 1.5 to 2.5;
   d is an integer ranging from 6 to 12;
   n is an integer ranging from 11 to 14.

2. The water-in-oil sunscreen emulsion of claim 1 having an SE of at least 3.

3. The water-in-oil sunscreen emulsion of claim 1 having an SE of at least 4.

4. The water-in-oil sunscreen emulsion of claim 1 where the SPF X is at least 30.

5. The water-in-oil sunscreen emulsion of claim 2 where the SPF X is at least 30.

6. The water-in-oil sunscreen emulsion of claim 3 where the SPF X is at least 30.

7. The water-in-oil sunscreen emulsion of claim 1 where the effective emulsifying concentration of the alkyl dimethicone copolyol of Formula A is from about 1% to about 10%.

8. The water-in-oil sunscreen emulsion of claim 7 where the effective emulsifying concentration of the alkyl dimethicone copolyol of Formula A is from about 3% to about 7%.

9. The water-in-oil sunscreen emulsion of claim 7 where the effective emulsifying concentration of the alkyl dimethicone copolyol of Formula A is from about 4.5% to about 5.5%.

10. The water-in-oil sunscreen emulsion of claim 1 where the at least one sunscreen active absorbs UVB radiation.

11. The water-in-oil sunscreen emulsion of claim 1 where the at least one sunscreen active absorbs UVB radiation and UVA radiation.

12. The water-in-oil sunscreen emulsion of claim 1 where the at least one sunscreen active is a combination of at least one UVA sunscreen and at least one UVB sunscreen.

13. The water-in-oil sunscreen emulsion of claim 1 where the at least one UVA sunscreen and at least one UVB sunscreen are a photostable sunscreen combination.

14. The water-in-oil sunscreen emulsion of claim 13 where the photostable sunscreen combination comprises avobenzone, octocrylene and oxybenzone.

15. The water-in-oil sunscreen emulsion of claim 14 where the photostable sunscreen combination comprises avobenzone, octocrylene and oxybenzone in a ratio of a:b:c, where a is from 0.5 to 5, b is from 0.5 to 10, and c is from 0.5 to 10.

16. The composition of claim 15 wherein avobenzone, oxybenzone, octocrylene are present in a ratio a:b:c, where a is from 1 to 3, b is from 1 to 6, and c is from 1 to 10.

17. The water-in-oil sunscreen emulsion of claim 2 where the at least one sunscreen active is a combination of at least one UVA sunscreen and at least one UVB sunscreen.

18. The water-in-oil sunscreen emulsion of claim 3 where the at least one sunscreen active is a combination of at least one UVA sunscreen and at least one UVB sunscreen.

19. The water-in-oil sunscreen emulsion of claim 4 where the at least one sunscreen active is a combination of at least one UVA sunscreen and at least one UVB sunscreen.

20. The water-in-oil sunscreen emulsion of claim 5 where the at least one sunscreen active is a combination of at least one UVA sunscreen and at least one UVB sunscreen.

21. The water-in-oil sunscreen emulsion of claim 6 where the at least one sunscreen active is a combination of at least one UVA sunscreen and at least one UVB sunscreen.

22. The water-in-oil sunscreen emulsion of claim 17 where the at least one UVA sunscreen and at least one UVB sunscreen are a photostable sunscreen combination.

23. The water-in-oil sunscreen emulsion of claim 18 where the at least one UVA sunscreen and at least one UVB sunscreen are a photostable sunscreen combination.

24. The water-in-oil sunscreen emulsion of claim 19 where the at least one UVA sunscreen and at least one UVB sunscreen are a photostable sunscreen combination.

25. The water-in-oil sunscreen emulsion of claim 20 where the at least one UVA sunscreen and at least one UVB sunscreen are a photostable sunscreen combination.

26. The water-in-oil sunscreen emulsion of claim 21 where the at least one UVA sunscreen and at least one UVB sunscreen are a photostable sunscreen combination.

27. The water-in-oil sunscreen emulsion of claim 22 where the photostable sunscreen combination comprises avobenzone, octocrylene and oxybenzone.

28. The water-in-oil sunscreen emulsion of claim 23 where the photostable sunscreen combination comprises avobenzone, octocrylene and oxybenzone.

29. The water-in-oil sunscreen emulsion of claim 24 where the photostable sunscreen combination comprises avobenzone, octocrylene and oxybenzone.

30. The water-in-oil sunscreen emulsion of claim 25 where the photostable sunscreen combination comprises avobenzone, octocrylene and oxybenzone.

31. The water-in-oil sunscreen emulsion of claim 26 where the photostable sunscreen combination comprises avobenzone, octocrylene and oxybenzone.

32. The composition of claim 1 further comprising one or more diluents selected from the group of rheology modifiers, emulsifiers, pH modifiers, moisturizers, humectants, emollients, stabilizers, lubricants, fragrances, preservatives, colored pigments and coloring agents.

33. The composition of claim 1 wherein the composition form is a lotion, cream, spray, gel, wax-type stick, oil, milk or mousse.

34. A method of protecting the skin from damage caused by ultraviolet radiation comprising applying the formulation of claim 1 to the skin.

35. A method of protecting the skin from damage caused by ultraviolet radiation comprising applying the formulation of claim 2 to the skin.

36. A method of protecting the skin from damage caused by ultraviolet radiation comprising applying the formulation of claim 3 to the skin.

37. A method of protecting the skin from damage caused by ultraviolet radiation comprising applying the formulation of claim 4 to the skin.

38. A method of protecting the skin from damage caused by ultraviolet radiation comprising applying the formulation of claim 5 to the skin.

39. A method of protecting the skin from damage caused by ultraviolet radiation comprising applying the formulation of claim 6 to the skin.

* * * * *